United States Patent [19]
Gatlin et al.

[11] Patent Number: 5,866,591
[45] Date of Patent: Feb. 2, 1999

[54] STABLE FORMULATIONS OF REMIFENTANIL

[75] Inventors: Larry Alan Gatlin, Chapel Hill; Shirley Ann Heiman; Janet Sue Lewis, both of Cary, all of N.C.

[73] Assignee: Glaxo Wellcome Inc., Research Triangle Park, N.C.

[21] Appl. No.: 926,930

[22] Filed: Sep. 10, 1997

Related U.S. Application Data

[60] Provisional application No. 60/025,940 Sep. 11, 1996.

[51] Int. Cl.$^6$ .................................................. A61K 31/445
[52] U.S. Cl. ........................... 514/329; 514/561; 546/224
[58] Field of Search ..................... 514/329, 561; 546/224

[56] References Cited

U.S. PATENT DOCUMENTS

| | | |
|---|---|---|
| 5,019,583 | 5/1991 | Feldman et al. . |
| 5,039,804 | 8/1991 | Feldman et al. . |
| 5,126,455 | 6/1992 | Feldman et al. . |
| 5,268,368 | 12/1993 | Palepu . |
| 5,466,700 | 11/1995 | Batenhorst et al. . |

FOREIGN PATENT DOCUMENTS 0 638554B1 2/1995 European Pat. Off. .

OTHER PUBLICATIONS

Akers et al., Glycine Crystallization During Freezing: The Effects of Salt Form, pH, and Ionic Strength, *Pharmacuetical Research*, vol. 12, No. 10, pp. 1457–1461 (1995).

Feldman et al., Design, Synthesis, and Pharmacological Evaluation of Ultrashort—to Long–Acting Opioid Analgetics, *Journal of Medicinal Chemistry*, 1991, vol. 34, No. 7, pp. 2202–2208.

James et al., Opioid Receptor Activity of GI 87084B, a Novel Ultra–Short Acting Analgesic, in Isolated Tissues, *Journal of Pharmacology and Experimental Therapeutics* , 1991 vol. 259, No. 2, pp. 712–718.

Lutz et al., A Pharmacodynamic Model to Investigate the Structure–Activity Profile of a Series of Novel Opioid Analgesics, *Journal of Pharmacology and Experimental Therapeutics*, 1994, vol. 271, No. 2, pp. 795–803.

Remifentanil Hydrochloride, *Drugs of the Future 1994*, 19(12)pp. 1088–1092.

Remifentanil Hydrochloride Ultiva, *Drugs of the Future 1995*, 20(12) pp. 1296–1298.

Amin et al., Naloxone Reversal of Depressed Ventilatory Response to Hypoxia During Continuous Infusion of Remifentanil, *Anesthesiology*, V.79, No. 3A, Sep. 1993, A1203.

Amin et al., Naloxone–Induced and Spontaneous reversal of Depressed Ventilatory Responses to Hypoxia during and after Continuous Infusion of Remifentanil or Alfentanil, *Journal of Phamacology and Experimental Therapeutics*, vol. 274, No. 1, 1995, pp. 34–39.

Zadeii et al., Stability of Ethiofos (NSC–29691) in Aqueous Solution and Solid Phase Formulation Pharmaceutical Research, vol. 8, No. 10, 1991, pp. S172, PDD7184./

Korey et al., Effects of Excipients on the Crystallization of Pharmaceutical Compounds During Lyophilization, *Journal of Parenteral Science & Technology*, vol. 43, No. 2, Mar.–Apr. 1, 1989.

Bashir et al., Evaluation of Freeze–Dried Products for Injection, *Bulletin of Parenteral Association*, vol. 27, No. 2, Mar.–Apr. 1973, pp. 68–83.

Wang et al., Parenteral Formulations of Proteins and Peptides: Stability and Stabilizers, *Parenteral Science and Technology*, vol. 42, No. 2S, 1988 Supplement, Tech. Report No. 10.

Nail et al., Freeze Drying: Principles and Practice, *Pharmaceutical Dosage Forms–Parenteral Medications*, 2nd Edition, vol. 2, 1993, pp. 163–233.

"Tablet Formulation and Design", *Pharmaceutical Dosage Forms–Tablets*, 2nd Edition, vol. 1, 1989, p. 105.

Ash et al., *Handbook of Pharmaceutical Additives*, 1995, p. 524.

*Primary Examiner*—Rebecca Cook
*Attorney, Agent, or Firm*—Shah R. Makujina; Robert H. Brink

[57] ABSTRACT

Stable formulations of 3-[4-methoxycarbonyl-4-[(1-oxopropyl)phenylamino]-1-piperidine]propanoic acid, methyl ester, generally referred to as remifentanil, are disclosed. In particular, stabilized lyophilized solid composition are disclosed comprising certain acids, most preferably comprising glycine.

20 Claims, No Drawings

STABLE FORMULATIONS OF REMIFENTANIL

This application claims the benefit of priority under Title 35, United States Code δ119(e) of United States provisional application 60/025,940 filed Sep. 11, 1996.

FIELD OF THE INVENTION

The present invention relates to formulations of N-phenyl-N-(4-piperidinyl)amides. In particular, the present invention relates to compositions containing 3-[4-methoxycarbonyl-4-[(1 -oxopropyl)phenylamino]-1-piperidine]propanoic acid, methyl ester (remifentanil).

BACKGROUND

The hydrochloride salt of remifentanil is commercially available from GlaxoWellcome for use in anesthesia under the tradename ULTIVA™. See U.S. Pat. Nos. 5,019,583 (Feldman et al.) and 5,446,700 (Batenhorst et al.), both of which are hereby incorporated by reference. Remifentanil hydrochloride is a potent N-phenyl-N-(4-piperidinyl)amide mu-opioid anesthetic.

The drug substance contains two alkyl esters, one sterically hindered and the other sterically unhindered and thought to be susceptible to hydrolysis (Scheme 1). The sterically unhindered ester grouping is thought to be highly susceptible to hydrolysis by aqueous hydrolysis and by esterases in blood and tissues. The major hydrolysis product is the monocarboxylic acid which is significantly less potent than remifentanil. Remifentanil hydrochloride exhibits a rapid onset of action and rapid recovery.

The rapid inactivation of remifentanil by hydrolysis provides the following advantages in anesthesia: 1) an ultra-short duration of action; 2) less variability in recovery rate even with differences in hepatic function; 3) no accumulation of drug during repeated bolus doses or infusion; and 4) more rapid recovery.

DESCRIPTION OF THE INVENTION

Remifentanil generally exists in one of two forms, it is either unprotonated (the free base), or it is protonated and accompanied by an appropriate counter ion, for example chloride, as in remifentanil hydrochloride. As used herein, "remifentanil" can refer to either form. When a specific form is intended, "remifentanil" will be modified appropriately as either the free base or as whichever particular salt is referred to, for example remifentanil hydrochloride or remifentanil glycinate. Similarly, glycine can exist as a neutral molecule or as a cation or anion with appropriate counter ion. Unless indicated otherwise, reference to "glycine" herein includes any such form of glycine. For example, a reference to a composition of remifentanil, glycine, and HCl would, unless otherwise indicated, include a composition of remifentanil glycinate (Scheme 4). Remifentanil glycinate is a salt of protonated remifentanil and anionic glycine.

When discussing the pH of solid compositions herein, we are referring to the pH of an aqueous solution resulting from dissolving the solid composition in an amount of aqueous liquid suitable for intravenous administration to a patient.

The present invention provides a solid composition comprising remifentanil that maintains a room temperature shelf life stability of two years (i.e., degrades to an extent of less than 10% in two years). Preferred solid compositions are lyophilized solid compositions.

Preferred compositions of this invention comprise remifentanil and at least one of the following agents: ascorbic acid, citric acid, maleic acid, phosphoric acid glycine, glycine hydrochloride, the combination of glycine and hydrochloric acid, succinic acid, or tartaric acid. These agents are believed to be useful as buffering, caking, or visualization agents. Most preferably, the compositions comprise glycine, glycine hydrochloride, or the combination of glycine and hydrochloric acid. In some cases it may be beneficial to also have some sodium chloride, mannitol, polyvinylpyrrolidone, or other ingredients in the compositions. Preferably, in the compositions of this invention which comprise remifentanil and glycine, remifentanil and glycine comprise at least 20%, more preferably at least 50% by weight of the. Preferably the compositions of this invention contain less than 3% of water.

The compositions of this invention provide stable formulations of remifentanil and they may also be used to reduce the pH of typical infusion solutions. The composition of this invention are buffered to a range of pH 1.5–pH 5, or more preferably to a pH range of pH 2.5–pH 3.5, or most preferably to a pH range of pH 2.8–pH 3.2. That is, they give a solution in the stated pH ranges when dissolved in an amount of water to give a composition suitable for intravenous administration to a patient. Typically the diluted solutions suitable for administration will contain from 1 mg remifentanil per 10 to 1,000 mL of solution. For example, certain glycine-containing compositions of this invention prepared to give solutions with an initial pH range of pH 2.8–pH 3.2, still gave solutions with a pH range of pH 2.5–pH 3.5 after storage at room temperature for at least two years.

It may be that the stability of the compositions of this invention is the result of the formation of stable complexes, for example a complex of remifentanil hydrochloride, glycine, and water. Such a complex may be a 1:1:1 complex of remifentanil hydrochloride, glycine, and water as illustrated in Scheme 2 or it may a 2:2:2 complex of remifentanil hydrochloride, glycine, and water as illustrated in Scheme 3.

The compositions of this invention may be lyophilized compositions or they may be simply solid mixtures or blends.

The excipient to drug ratio in the compositions of this invention are preferably no greater that 75 to 1 by weight, more preferably no greater than 40 to 1 by weight. The word excipient is meant to include all components other that the active drug substance.

The compositions of this invention can be sterilized, for example using gamma irradiation. Surprisingly, in the compositions of this invention, the drug is not significantly degraded by gamma irradiation.

Because of its high potency and propensity for rapid selective ester hydrolysis resulting in deactivation, remifentanil presents some unique challenges in devising commercially viable, room temperature shelf-stable formulations. The dosage forms are so low (1–5 milligrams) that accurate weighing of sterile crystalline drug substance is difficult. Liquid compositions, particularly aqueous solutions, are unlikely to be stable due to the ability for remifentanil hydrochloride to rapidly dissolve and hydrolyze in aqueous solutions.

The compositions of this invention are solid compositions. Dry powder blends can be prepared. However, uniformity of mixing of this highly potent drug substance in a dry powder blend and sterilization presents significant operational challenges. Particularly preferred compositions of this invention are lyophilized powders for reconstitution.

In use, the compositions of this invention are diluted with isotonic saline, or other suitable iv fluids, and then administered intravenously to the patient. Preferred iv fluids are those that do not adversely affect the buffer. Ringer's lactate solution is not preferred.

EXPERIMENTAL

A number of early lyophilized formulations were produced and studied. Surprisingly, the more common buffering systems such as ascorbic acid—sodium ascorbate, citric acid—sodium citrate, succinic acid—sodium succinate, tartaric acid—sodium tartrate, and the more common bulking or cake forming or visualizing agents such as lactose and mannitol all appeared to decrease the stability of remifentanil hydrochloride. Based on these data, it was then decided to use glycine (either neutral glycine, glycine hydrochloride, or both) and HCl as a buffering system. Using the glycine and HCl buffering system, and with mannitol as the caking agent, produced a workable formulation with a shelf life of three months when kept refrigerated at +4 degrees C. At room temperature this formulation degraded rapidly over a period of days with a new impurity forming in a time dependent manner. Replacing the mannitol caking agent with sodium chloride also did not provide a suitable room-temperature shelf-stable cake.

However, when the glycine and HCl buffering system was employed over a narrow pH range with excess glycine, remarkable and unexpectedly stable formulations resulted. These lyophilized powders contain less than 3% water, but provide the desired room temperature shelf life stability of at least two years. Additionally, these lyophilized powders possess high surface areas, allowing rapid reconstitution with a variety of sterile aqueous intravenous solutions.

Compositions of this invention are illustrated in the following non-limiting examples. Remifentanil and remifentanil hydrochloride can be prepared as described in European Patent Application EP 0638554 (D. W. S. Latham et al.) and the '583 and '700 patents cited above.

EXAMPLE 1

In this experiment the pH Rate Profile and Degradation Kinetics for Remifentanil Hydrochloride were studied. The hydrolysis of remifentanil hydrochloride to the corresponding monocarboxylic acid (Scheme 1) was characterized as a function of pH at +30 degrees C. All commercial buffers were adjusted to an ionic strength of 0.15 using sodium chloride. Samples at pH >7 were quenched with dilute hydrochloric acid to slow degradation prior to analysis of remifentanil by reverse phase high performance liquid chromatography (RP-HPLC). The rate constants (k) and time for 10% degradation ($t_{90}$) are shown below:

| pH   | Buffer        | k (day$^{-1}$) | $t_{90}$ |
|------|---------------|----------------|----------|
| 1.0  | 0.1M HCl      | 0.118          | 1 day    |
| 1.0  | 0.1M HCl      | 0.106          | 1 day    |
| 2.0  | 0.01M HCl     | 0.0130         | 8 days   |
| 2.0  | 0.01M HCl     | 0.0127         | 8 days   |
| 2.6  | 0.01M formate | 0.00760        | 14 days  |
| 3.0  | 0.05M citrate | 0.00567        | 19 days  |
| 3.0  | 0.05M glycine | 0.00403        | 26 days  |
| 3.7  | 0.01M citrate | 0.00451        | 23 days  |
| 4.0  | 0.05M citrate | 0.0130         | 8 days   |
| 4.0  | 0.05M succinate | 0.0130       | 8 days   |
| 4.3  | 0.01M acetate | 0.0148         | 7 days   |
| 5.0  | 0.045M citrate | 0.0818        | 1 day    |
| 5.0  | 0.05M succinate | 0.0833       | 1 day    |
| 6.0  | 0.05M succinate | 0.617        | 4 hrs.   |
| 6.0  | 0.05M maleate | 0.688          | 4 hrs.   |

-continued

| pH   | Buffer          | k (day$^{-1}$) | $t_{90}$ |
|------|-----------------|----------------|----------|
| 7.0  | 0.05M imidazole | 3.46           | 44 min.  |
| 7.0  | 0.05M phosphate | 4.29           | 35 min.  |
| 7.7  | 0.05M imidazole | 6.63           | 23 min.  |
| 8.0  | 0.05M TRIS      | 7.49           | 20 min.  |
| 9.2  | 0.05M borate    | 10.1           | 15 min.  |
| 10.9 | 0.05M borate    | 13.8           | 11 min.  |
| 11.0 | 0.05M carbonate | 36.4           | 4 min.   |
| 11.5 | 0.03M phosphate | 110            | 1 min.   |

EXAMPLE 2

In this example a citric acid dry powder blend was prepared. Solid samples of 22 milligrams of remifentanil hydrochloride, 4.725 grams of citric acid and 1.575 grams of sodium citrate were intimately mixed with a mortar and pestle. A total of 300 milligrams of this formulation was then placed in a 5 mL glass vial, sealed with a closure and stored at +40 degrees C. for one month. Analysis by reverse phase high performance liquid chromatography (RP-HPLC) indicated 95% loss of active drug substance (i.e., only 5% of the initial analysis remained).

EXAMPLE 3

In this example a tartaric acid dry powder blend was prepared. Solid samples of 22 milligrams of remifentanil hydrochloride, 3.150 grams of tartaric acid and 3.150 grams of sodium tartrate were intimately mixed with a mortar and pestle. A total of 300 milligrams of this formulation was then placed in a 5 mL glass vial, sealed with a closure and stored at +40 degrees C. for one month. Analysis by reverse phase high performance liquid chromatography (RP-HPLC) indicated 95% loss of active drug substance (5% of initial analysis remained).

EXAMPLE 4

In this example a succinic acid dry powder blend was prepared. Solid samples of 22 milligrams of remifentanil hydrochloride, 5.775 grams of succinic acid and 0.530 gram of sodium succinate were intimately mixed with a mortar and pestle. A total of 300 milligrams of this formulation was then placed in a 5 mL glass vial, sealed with a closure and stored at +40 degrees C. for one month. Analysis by reverse phase high performance liquid chromatography (RP-HPLC) indicated 75% loss of active drug substance (25% of initial analysis remained).

EXAMPLE 5

In this example a glycine dry powder blend was prepared. Solid samples of 22 milligrams of remifentanil hydrochloride, 4.725 grams of glycine and 1.575 grams of glycine hydrochloride were intimately mixed with a mortar and pestle. A total of 300 milligrams of this formulation was then placed in a 5 mL glass vial, sealed with a closure and stored at +40 degrees C. for one month. Analysis by reverse phase high performance liquid chromatography (RP-HPLC) indicated no loss of active drug substance (100% of initial analysis remained).

EXAMPLE 6

In this example a sodium chloride dry powder blend was prepared. Solid samples of 22 mg of remifentanil hydrochloride and 6.3 grams of sodium chloride were intimately mixed with a mortar and pestle. A total of 300 milligrams of this formulation was then placed in a 5 mL glass vial, sealed with a closure and stored at +40 degrees C. for one month. Analysis by reverse phase high performance liquid chromatography (RP-HPLC) indicated 0.9% loss of active drug substance (99.1% of initial analysis remaining).

EXAMPLE 7

In this example a gamma irradiation of remifentanil hydrochloride was performed. Quantities of 1.655 milligrams, 1.809 milligrams, 2.355 milligrams and 4.283 milligrams of remifentanil hydrochloride were individually placed into four 2 mL glass vials which were then sealed. The sealed vials were individually exposed to 2.5 Mrads of gamma radiation from a cobalt 60 source. Samples of the irradiated drug substance were dissolved in 0.001N aqueous hydrochloric acid and assayed using reverse phase high performance liquid chromatography (RP-HPLC). Analysis revealed 1% or less loss of active drug substance (99–100% of initial analysis remained).

EXAMPLE 8

In this example an ascorbic acid lyophilized dosage form was prepared. Approximately 1 mL of water, 10 mg of ascorbic acid, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 16% loss of active drug substance (84% of initial analysis remains).

EXAMPLE 9

In this example a citric acid lyophilized dosage form was prepared. Approximately 1 mL of water, 10 mg of citric acid, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 14% loss of active drug substance (86% of initial analysis remained).

EXAMPLE 10

In this example a tartaric acid lyophilized dosage form was prepared. Approximately 1 mL of water, 10 mg of tararic acid, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 42% loss of active drug substance (58% of initial analysis remained).

EXAMPLE 11

In this example a lactose lyophilized dosage form was prepared. Approximately 1 mL of water, 10 mg of lactose, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 5% loss of active drug substance (95% of initial analysis remained).

EXAMPLE 12

In this example a mannitol lyophilized dosage form was prepared. Approximately 1 mL of water, 10 mg of mannitol, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 4% loss of active drug substance (96% of initial analysis remained).

EXAMPLE 13

In this example a PVP K-12 lyophilized dosage form was prepared. Approximately 1 mL of water, 10 mg of polyvinylpyrolidone commercial composition PVP K-12 (from BASF corporation), and 2.5 mg of remifentanil were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 4% loss of active drug substance (96% of initial analysis remained).

EXAMPLE 14

In this example a PVP K-17 lyophilized dosage form was prepared. Approximately 1 mL of water, 10 mg of polyvinylpyrolidone commercial composition PVP K-17 (from BASF corporation), and 2.5 mg of remifentanil were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 1% loss of active drug substance (99% of initial analysis remained).

EXAMPLE 15

In this example a sodium chloride lyophilized dosage form was prepared. Approximately 1 mL of water, 10 mg of sodium chloride, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated no loss of active drug substance (100% of initial analysis).

EXAMPLE 16

In this example a glycine lyophilized dosage form was prepared. Approximately 1 mL of water, 10 mg of glycine, and 2.5 mg of remifentanil hydrochloride were mixed to give a solution. The pH of this solution was adjusted to approximately pH 3 with 0.001N hydrochloric acid. This solution was placed into a 5 mL vial and lyophilized using a conservative cycle. The vial contents were lyophilized at a temperature beginning at −50 degrees C. and slowly warming the lyophilizer shelves to +30 degrees C. under a 150 micron vacuum. Lyophilization was complete after approximately 24 hours.

The lyophilized formulation was stored at +40 degrees C. for 1 month. Analysis by reverse phase high performance liquid chromatography (RP-HPLC) indicated 1% loss of active drug substance (99% of initial analysis).

EXAMPLES 17–19

In these examples various compositions containing glycine and mannitol were prepared and lyophilized.

In Example 17 approximately 1 mL of water, 15 mg of glycine, 60 mg of mannitol, and 0.1 mg of remifentanil hydrochloride were mixed to give a solution (excipient to drug ratio 750). The pH of this solution was adjusted to approximately pH 3 with 0.001N hydrochloric acid. This solution was placed into a 5 mL vial and lyophilized using a conservative cycle. The vial contents were lyophilized at a temperature beginning at below −40 degrees C. and slowly warming the lyophilizer shelves to +30 degrees C. under a 150 micron vacuum. Lyophilization was complete after approximately 24 hours. The lyophilized formulation was stored at +40 degrees C. for 1 month. Analysis by reverse phase high performance liquid chromatography (RP-HPLC) indicated 55% loss of active drug substance (45% of initial analysis remained).

In Example 18, the above experiment was repeated with 1 mL water, 15 mg of glycine, 40 mg of mannitol, and 0.2 mg of remifentanil hydrochloride (excipient to drug ratio 275) and the mixture lyophilized, stored, and analyzed in a similar manner, the reverse phase high performance liquid chromatography (RP-HPLC) indicated 13% loss of active drug substance (87% of initial analysis remained).

In example 19, the above experiment was repeated with 1 mL water, 15 mg of glycine, 60 mg of mannitol, and 1.0 mg of remifentanil hydrochloride (excipient to drug ratio 75) and the mixture lyophilized, stored, and analyzed in a similar manner, the reverse phase high performance liquid chromatography (RP-HPLC) indicated 6% loss of active drug substance (94% of initial analysis remained).

EXAMPLE 20

In this example a 1 mg remifentanil hydrochloride lyophilized dosage form was prepared. Approximately 85 liters of Water For Injection USP was added into a compounding vessel and 1.650 kilograms of glycine USP was dissolved with agitation. Sufficient dilute aqueous hydrochloric acid NF was added to the solution until the pH was approximately pH 3.1 (range pH 3.0–pH 3.5). A total of 121.6 grams of remifentanil hydrochloride was dispersed in a minimal volume of Water For Injection USP and transferred to the compounding vessel. This dispersion was mixed by agitation until all solids had dissolved. The final pH of the solution was adjusted to pH 3.0 (range pH 2.8–pH 3.2) with the addition of additional dilute aqueous hydrochloric acid NF. Sufficient Water For Injection USP was added to bring the final volume to 110.0 liters.

The bulk solution of remifentanil hydrochloride was filtered through a sterilizing-grade membrane filter and collected in a sterilized holding vessel. An automated filling unit dispensed 1.0 mL of the 1.0 mg/mL solution of remifentanil hydrochloride into glass vials. The filled vials were partially stoppered and loaded into a sterilized lyophilizer. The vials were lyophilized at a temperature beginning at −45 degrees C. and slowly warming the lyophilizer shelves to +40 degrees C. under a 250 micron vacuum. Lyophilization was complete after approximately 14 hours. The stable lyophilized formulation of remifentanil hydrochloride contained less than 3% water (weight/weight % basis). Analysis by reverse phase high performance liquid chromatography (RP-HPLC) indicated no detectable loss of active drug substance (100% of initial analysis remained). Stability studies showed that this formulation maintained a room temperature shelf life stability of two years (i.e. the drug substance remifentanil hydrochloride degraded by hydrolysis to an extent of less than 10% in two years).

EXAMPLE 21

In this example a 2 mg remifentanil hydrochloride lyophilized dosage form was prepared. Approximately 85 liters of Water For Injection USP was added into a compounding vessel and 1.650 kilograms of glycine USP was dissolved with agitation. Sufficient dilute aqueous hydrochloric acid NF was added to the solution until the pH was approximately pH 3.1 (range pH 3.0–pH 3.5). A total of 243.3 grams of remifentanil hydrochloride was dispersed in a minimal volume of Water For Injection USP and transferred to the compounding vessel. This dispersion was mixed by agitation until all solids had dissolved. The final pH of the solution was adjusted to pH 3.0 (range pH 2.8–pH 3.2) with the addition of additional dilute aqueous hydrochloric acid NF. Sufficient Water For Injection USP was added to bring the final volume to 110.0 liters.

The bulk solution of remifentanil hydrochloride was filtered through a sterilizing-grade membrane filter and collected in a sterilized holding vessel. An automated filling unit dispensed 1.0 mL of the 2.0 mg/mL solution of remifentanil hydrochloride into glass vials. The filled vials were partially stoppered and loaded into a sterilized lyophilizer. The vials were lyophilized at a temperature beginning at −45 degrees C. and slowly warming the lyophilizer shelves to +40 degrees C. under a 250 micron vacuum. Lyophilization was complete after approximately 14 hours. The stable lyophilized formulation of remifentanil hydrochloride contained less than 3% water (weight/weight % basis). Analysis by reverse phase high performance liquid chromatography (RP-HPLC) indicated no loss of active drug substance (100% of initial analysis). Stability studies showed that this formulation maintained a room temperature shelf life stability of two years (i.e. the drug substance remifentanil hydrochloride degraded by hydrolysis to an extent of less than 10% in two years).

EXAMPLE 22

In this example a 5 mg remifentanil hydrochloride lyophilized dosage form was prepared. Approximately 60 liters of Water For injection USP was added into a compounding vessel and 1.125 kilograms of glycine USP was dissolved with agitation. Sufficient dilute aqueous hydrochloric acid NF was added to the solution until the pH was approximately pH 3.1 (range pH 3.0–pH 3.5). A total of 414.7 grams of remifentanil hydrochloride was dispersed in a minimal volume of Water For Injection USP and transferred to the compounding vessel. This dispersion was mixed by agitation until all solids had dissolved. The final pH of the solution was adjusted to pH 3.0 (range pH 2.8–pH 3.2) with the addition of additional dilute aqueous hydrochloric acid NF. Sufficient Water For Injection USP was added to bring the final volume to 75.0 liters.

The bulk solution of remifentanil hydrochloride was filtered through a sterilizing-grade membrane filter and collected in a sterilized holding vessel. An automated filling unit dispensed 1.0 mL of the 5.0 mg/mL solution of remifentanil hydrochloride into glass vials. The filled vials were partially stoppered and loaded into a sterilized lyophilizer. The vials were lyophilized at a temperature beginning at −45 degrees C. and slowly warming the lyophilizer shelves to +40 degrees C. under a 250 micron vacuum. Lyophilization was complete after approximately 14 hours. The stable lyophilized formulation of remifentanil hydrochloride contained less than 3% water (weight/weight % basis). Analysis by reverse phase high performance liquid chromatography (RP-HPLC) indicated no loss of active drug substance (100% of initial analysis). Stability studies showed that this formulation maintained a room temperature shelf life stability of two years (i.e. the drug substance remifentanil hydrochloride degraded by hydrolysis to an extent of less than 10% in two years).

SCHEME 1
HYDROLYSIS OF REMIFENTANIL
AND REMIFENTANIL HYDROCHLORIDE

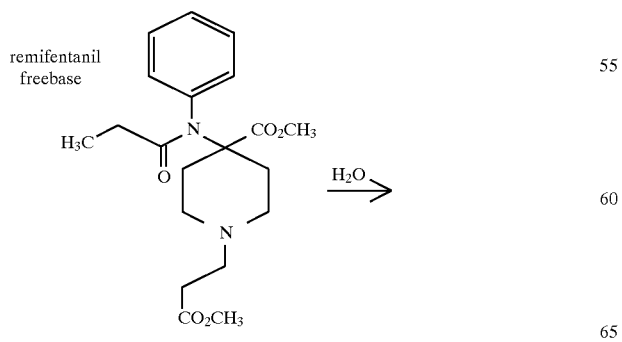

remifentanil freebase

-continued
SCHEME 1
HYDROLYSIS OF REMIFENTANIL
AND REMIFENTANIL HYDROCHLORIDE

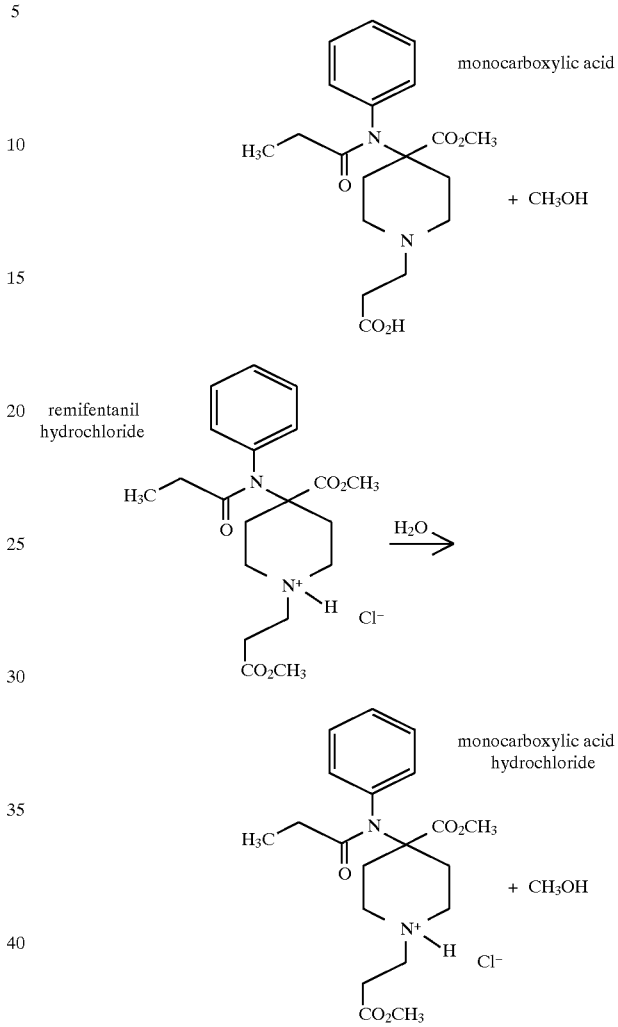

SCHEME 2
POSSIBLE 1:1:1 COMPLEXES OF REMIFENTANIL
HYDROCHLORIDE, GLYCINE AND WATER

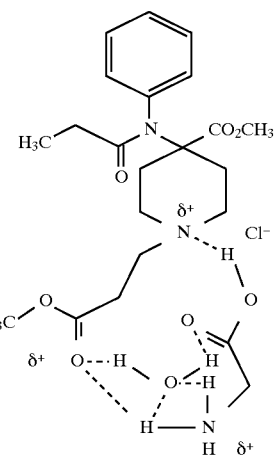

SCHEME 2
POSSIBLE 1:1:1 COMPLEXES OF REMIFENTANIL HYDROCHLORIDE, GLYCINE AND WATER

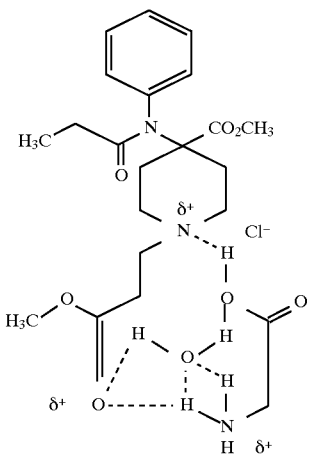

SCHEME 3
POSSIBLE 2:2:2 COMPLEX OF REMIFENTANIL HYDROCHLORIDE, GLYCINE AND WATER

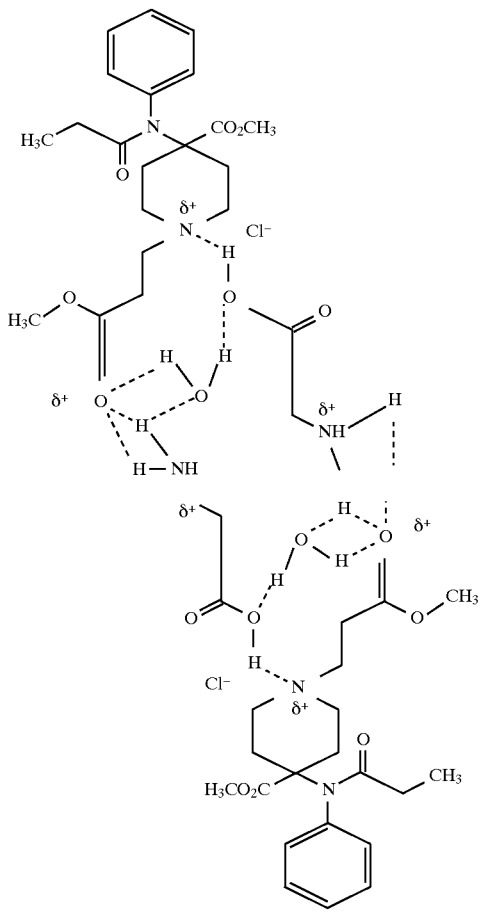

SCHEME 4
EQUILIBRIUM OF REMIFENTANIL AND GLYCINE - REMIFENTANIL GLYCINATE

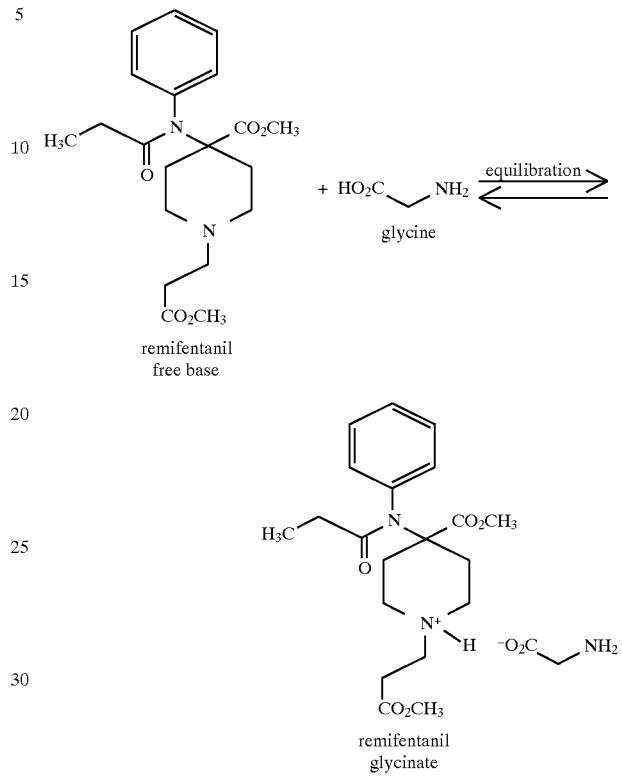

What is claimed is:

1. A solid composition comprising remifentanil and glycine, wherein said composition maintains a room temperature shelf life stability of at least two years.

2. The composition of claim 1 wherein said composition is a lyophilized solid composition.

3. A solid composition comprising remifentanil and at least one agent selected from the group consisting of ascorbic acid, citric acid, maleic acid, phosphoric acid, glycine, succinic acid, or tartaric acid.

4. The composition of claim 3 wherein said composition comprises less than 3% by weight water.

5. The composition of claim 3 wherein said agent is glycine.

6. The composition of claim 5 further comprising sodium chloride, polyvinylpyrolidone, or mannitol.

7. The composition of claim 5 wherein remifentanil and glycine comprise at least 20% by weight of the composition.

8. The composition of claim 5 wherein remifentanil and glycine comprise at least 50% by weight of the composition.

9. The composition of claim 5 wherein said composition gives an aqueous solution having a pH of from pH 1.5 to pH 5, when dissolved in an amount of aqueous liquid to give a composition suitable for intravenous administration to a patient.

10. The composition of claim 5 wherein said composition gives an aqueous solution having a pH of from pH 2.5 to pH 3.5, when dissolved in an amount of aqueous liquid to give a composition suitable for intravenous administration to a patient.

11. The composition of claim 5 wherein said composition gives an aqueous solution having a pH of from pH 2.8 to pH 3.2, when dissolved in an amount of aqueous liquid to give a composition suitable for intravenous administration to a patient.

12. The composition of claim 5 wherein said composition is lyophilized.

13. The composition of claim 12 wherein said composition is sterilized.

14. The composition of claim 5 wherein the ratio by weight of other components to remifentanil is less than or equal to 75 to 1.

15. The composition of claim 5 wherein the ratio by weight of other components to remifentanil is less than or equal to 40 to 1.

16. The composition of claim 5 wherein the ratio by weight of other components to remifentanil is less than or equal to 15 to 1.

17. The composition of claim 5 wherein glycine comprises at least 50% by weight of the composition.

18. The composition of claim 5 wherein said composition comprises, for each part by weight of remifentanil free base or hydrochloride salt, from 2 to 20 parts by weight of glycine, and from 0 to 50 parts by weight of other ingredients.

19. A complex of remifentanil hydrochloride, glycine, and water.

20. Remifentanil glycinate.

\* \* \* \* \*